United States Patent [19]
Liedenbaum et al.

[11] Patent Number: 5,940,198
[45] Date of Patent: Aug. 17, 1999

[54] OPTICAL UNIT FOR SYNCHRONIZING CLOCK SIGNALS

[75] Inventors: Coen T.H.F. Liedenbaum; Engelbertus C.M. Pennings, both of Eindhoven, Netherlands; Raymond Van Roijen, Yorktown Heights, N.Y.; John J.E. Reid, Eindhoven, Netherlands; Lukas F. Tiemeijer, Eindhoven, Netherlands; Bastiaan H. Verbeek, Eindhoven, Netherlands

[73] Assignee: U.S. Philips Corporation, New York, N.Y.

[21] Appl. No.: 08/767,737

[22] Filed: Dec. 16, 1996

[30] Foreign Application Priority Data

Dec. 22, 1995 [EP] European Pat. Off. .............. 95203623

[51] Int. Cl.[6] .................................................. H04B 10/00
[52] U.S. Cl. ............................................................ 359/158
[58] Field of Search .................................... 359/158, 154; 372/94, 34; 375/354

[56] References Cited

U.S. PATENT DOCUMENTS 5,652,669   7/1997   Liedenbaum et al. .................. 359/158

FOREIGN PATENT DOCUMENTS 06069580   3/1994   Japan .

OTHER PUBLICATIONS

"Compact InP–Based Ring Lasers Employing Multimode Interference Couplers and Combiners", R. van Roijen et al, Appl. Phys. Lett 64, (14), Apr. 4, 1994, pp. 1753–1755.

"Ultra–High–SpeechPLL–Type Clock Recovery Circuit Based on All–Optical Gain Modulation in Traveling–Wave Laser Diode Amplifier", by S. Kawanishi et al, Journal of Lightwave Technology, vol. 11, No. 12, Dec. 1993, pp. 2123–2129.

"Frequency Multiplication in Activity Mode–Locked Semiconductor Lasers", by N. Onodera et al., Applied Physics Letter vol. 62, No. 12, Mar. 1993.

Primary Examiner—Kinfe-Michael Negash
Attorney, Agent, or Firm—Steven R. Biren

[57] ABSTRACT

The invention relates to an optical unit (17) for synchronizing clock signals. The unit (17) comprises at least two ring lasers (1', 1"), each ring laser (1', 1") generating a repetitive optical pattern at a different repetition frequency $f_i$. The repetition frequency of at least one of the ring lasers (1', 1") is variable. The unit (17) comprises detection means (19) adapted to simultaneously receive the optical patterns from two ring lasers (1', 1") to be synchronized with each other and to compare these patterns. The ring laser, whose repetition frequency is variable, is controllable on the basis of a signal from the detection means, by which the optical path length of this laser is changed. The invention also relates to a high-frequency carrier transmission system comprising an optical unit as described hereinbefore.

11 Claims, 5 Drawing Sheets

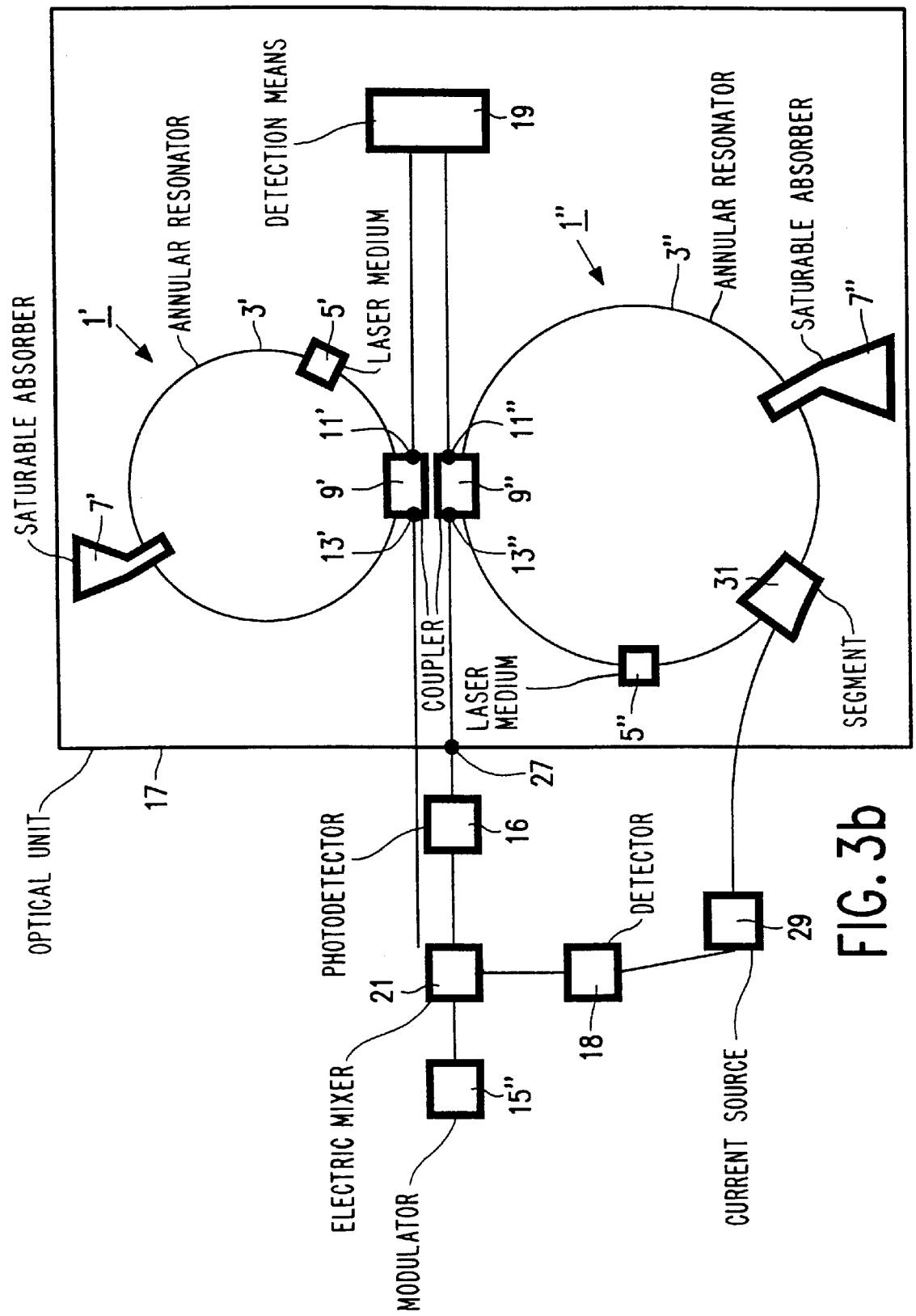

OPTICAL UNIT FOR SYNCHRONIZING CLOCK SIGNALS

BACKGROUND OF THE INVENTION

The invention relates to an optical unit for synchronizing clock signals. In systems operating with high frequency signals, i.e. signals having a frequency of more than 10 GHz, there is the problem that the current electronic components are not fast enough and are thus not satisfactory. 10 GHz may be considered as an electronic barrier. Moreover, these systems also comprise semiconductor lasers in many cases, which can generally be modulated to frequencies of 10–15 GHz maximum. Applications in which high-frequency signals are desired and will also play an important role in the future are, for example, satellite transmission, optical telecommunication and mobile telephony.

The invention also relates to a transmission system having high-frequency carrier waves, provided with such an optical unit.

SUMMARY OF THE INVENTION

It is an object of the invention to provide an optical unit with which it is possible to synchronize clock signals with each other and to generate high-frequency clock signals which are synchronized with low-frequency signals without the electronic components causing limitations.

To this end, the optical unit according to the invention comprises at least two ring lasers, each ring laser generating a repetitive optical pattern at a different repetition frequency $f_i$, which unit further comprises detection means adapted to simultaneously receive the optical patterns from two ring lasers to be synchronized with each other and to compare these patterns, wherein the repetition frequency of at least one of the ring lasers is variable on the basis of a signal from the detection means.

A repetitive optical pattern is understood to be a pattern which is identical at well-defined interval $T_i$. Its frequency is given by $f_i=1/T_i$.

A ring laser is known per se, for example from the article: "Compact InP-based ring lasers employing multimode interference couplers and combiners" by R. van Roijen et al. in Applied Physics Letters 64 (14), April 1994. The laser comprises an annular resonator, incorporating a laser medium, in the form of an active amplifier or an amplifying medium. When the laser medium is activated, radiation will be generated which propagates through the resonator. The ring is provided with a saturable absorber whose losses determine the laser action of the ring laser. Moreover, the ring incorporates a multimode interference (MMI) coupler ensuring that the radiation generated in the ring can also be coupled out. The operating principle of a ring laser is based on the fact that the position of the absorber in the ring does not play a role.

The laser structure described has the advantage with respect to the linear version of a CPM (Colliding Pulse Modelocked) laser that the location of the saturable absorber is not important, because it will always be located centrally in the resonator.

The repetition frequency of a ring laser is given by $f_{rep} \approx c/n.L$, in which c is the velocity of the light in the resonator medium, n is the refractive index and L is the length of the resonator. Consequently, the repetition frequency can be adapted by varying the optical path length n.L. In contrast to the electronic components, high frequencies can be realized more easily because small rings can be manufactured in a relatively simple manner.

By causing the pulses from the ring lasers which must be synchronized with each other to arrive simultaneously at the detection means, the difference in repetition frequency between these lasers can be measured as a difference frequency. The difference frequency should be within the bandwidth of the detection means. In this way, the lasers are not only adjusted in frequency but also in phase with each other. Simultaneously is to be understood to mean within a given time interval in which the repetitive pattern of each ring laser is present.

In a preferred embodiment of the optical unit according to the invention, the ring lasers associated with a pair to be synchronized have such a characteristic that it holds for the repetition frequencies $f_1$ and $f_2$ of these ring lasers that $k.f_1 \approx m.f_2$, in which k and m are integers.

When comparing two frequencies, a signal having the difference frequency is produced, which is referred to as a beat signal. An advantage thereof is that it is sufficient to use detection means for detecting frequencies which are much lower than those of the signals to be compared with each other, because the beat signal will have a very small repetition frequency. In this way, very high frequencies can be compared with each other, as long as multiples of these frequencies are to be found, between which the difference is small enough to be electrically detected.

In a further embodiment of the optical unit according to the invention, one of the ring lasers is coupled to an electric pulse-generating unit.

By connecting one of the ring lasers to the unit which supplies the electric signal, the original electric signal can be converted into an optical signal. Preferably, this is the ring laser having the lowest repetition frequency. Subsequently, the optical pulse series having a relatively low repetition frequency can be converted in one or more steps into an optical signal having a much higher repetition frequency. This relatively high repetition frequency will be synchronized with the original electric signal.

The optical signal supplied by the ring laser can be provided with the frequency of the electric signal by applying the frequency of the electric modulator directly to the resonator via a segment (current injection) without using feedback to adapt the electrical frequency to the optical frequency. In this way, the resonator is forced, as it were, to supply optical pulses at a given frequency. A condition is that the frequency of the electric signal and the frequency of the signal which the ring laser can generate itself, are not too far apart.

The electrical and optical pulse series may also be synchronized with each other in passive ways, using a feedback so as to adapt the repetition frequency of the ring laser to that of the electric signal.

In a first embodiment of the optical unit according to the invention, in which the synchronization takes place in a passive manner, an extent of radiation causing a charge carrier density change resulting in a change of the repetition frequency is injectable into the resonator of the ring laser which is coupled to the electric pulse-generating unit.

By injecting a high intensity radiation into the resonator, the charge carrier density will be influenced. At a sufficient change of the charge carrier density, the repetition frequency will change. By measuring the difference frequency between the electric signal and the optical signal generated by the ring laser, the intensity of the injected radiation can be corrected until a change of the charge carrier density is achieved for which the measured difference frequency, between the frequencies themselves or between the smallest common multiples thereof, is substantially equal to zero. The radiation may be injected, for example, via an extra coupler arranged in the resonator.

In a second embodiment of the optical unit according to the invention, in which the synchronization takes place in a passive manner, the resonator of the ring laser has an area in which current is injectable into the resonator.

Current can be injected into the resonator via a segment. As a result of this current injection, the optical path length will change.

In a third embodiment of the optical unit according to the invention, in which the synchronization takes place in a passive manner, the resonator is provided with means with which the temperature of the resonator is continuously variable.

The means may be constituted, for example by a Peltier element. Also by varying the temperature of the resonator, the optical path length and hence the repetition frequency will change. With reference to the measured difference frequency between the two signals to be synchronized, the required temperature change can be determined.

In contrast to the fact that the synchronization of an electric and an optical signal may be effected both actively and passively, the optical signals, each coming from a ring laser, may only be synchronized with each other in a passive manner, in other words by means of feedback.

In a first embodiment of the optical unit according to the invention, the detection means are constituted by a photodetector for measuring a difference frequency between the repetition frequencies or between smallest common multiples of the repetition frequencies of the two ring lasers to be synchronized with each other, the photodetector being connected to a conversion unit which in turn is coupled to a control unit for controlling a drive unit by means of which the optical path length of one of the ring lasers is variable.

The difference frequency will be measured by the photodetector, provided that the photodetector has a sufficient bandwidth for this purpose. The signal from the photodetector is converted in the conversion unit into a signal which will serve as a reference signal for the drive unit with which the optical path length of the ring laser is variable.

In a second embodiment of the optical unit according to the invention, the detection means comprise a unit in which the optical signals to be synchronized can be mixed to one signal having a frequency which is equal to the difference frequency between the signals to be mixed, said unit being connected to a conversion unit which in turn is coupled to a control unit for controlling a drive unit with which the optical path length of one of the ring lasers is variable.

The two optical signals, which must be synchronized with each other, can be combined to one signal having a frequency which is equal to the difference frequency of the two signals or equal to the difference between the smallest common multiples of the frequencies of the two signals. With reference to the value of this difference frequency, the ring laser whose repetition frequency must be adapted can be corrected in optical path length.

An example of an optical mixer which may be used for this purpose is described in the article: "Ultra-High-Speed PLL-Type Clock Recovery Circuit Based on All-Optical Gain Modulation in Traveling-Wave Laser Diode Amplifier" by Satoki Kawanishi et al. in Journal of Lightwave Technology, Vol. 11, No. 12, December 1993. The optical mixer may alternatively be implemented as an optical switch such as, for example, a NOLM (nonlinear optical loop mirror) or a SLALOM (semiconductor laser amplifier optical mirror) which are known per se.

The optical path length of one of the ring lasers is variable in the same manner as described for the synchronization between an electric and an optical signal, namely by means of current injection, radiation injection or temperature change.

In an embodiment of the optical unit according to the invention, an extent of radiation causing a charge carrier density change resulting in a change of the repetition frequency is injectable into the resonator of one of the ring lasers.

In another embodiment of the optical unit according to the invention, the resonator of one of the ring lasers has an area in which current is injectable into the resonator.

In yet another embodiment of the optical unit according to the invention, the resonator of one of the ring lasers is provided with means by which the temperature of the resonator is continuously variable.

These and other aspects of the invention will be apparent from and elucidated with reference to the embodiments described hereinafter.

BRIEF DESCRIPTION OF THE DRAWING

In the drawings:

FIGS. 3(a)–(c) show some embodiments of an optical unit according to the invention, provided with two ring lasers, in which one of the ring lasers is synchronized with the electric signal in a passive manner.

DETAILED DESCRIPTION OF THE PREFERRED EMBODIMENTS

Figure 1:
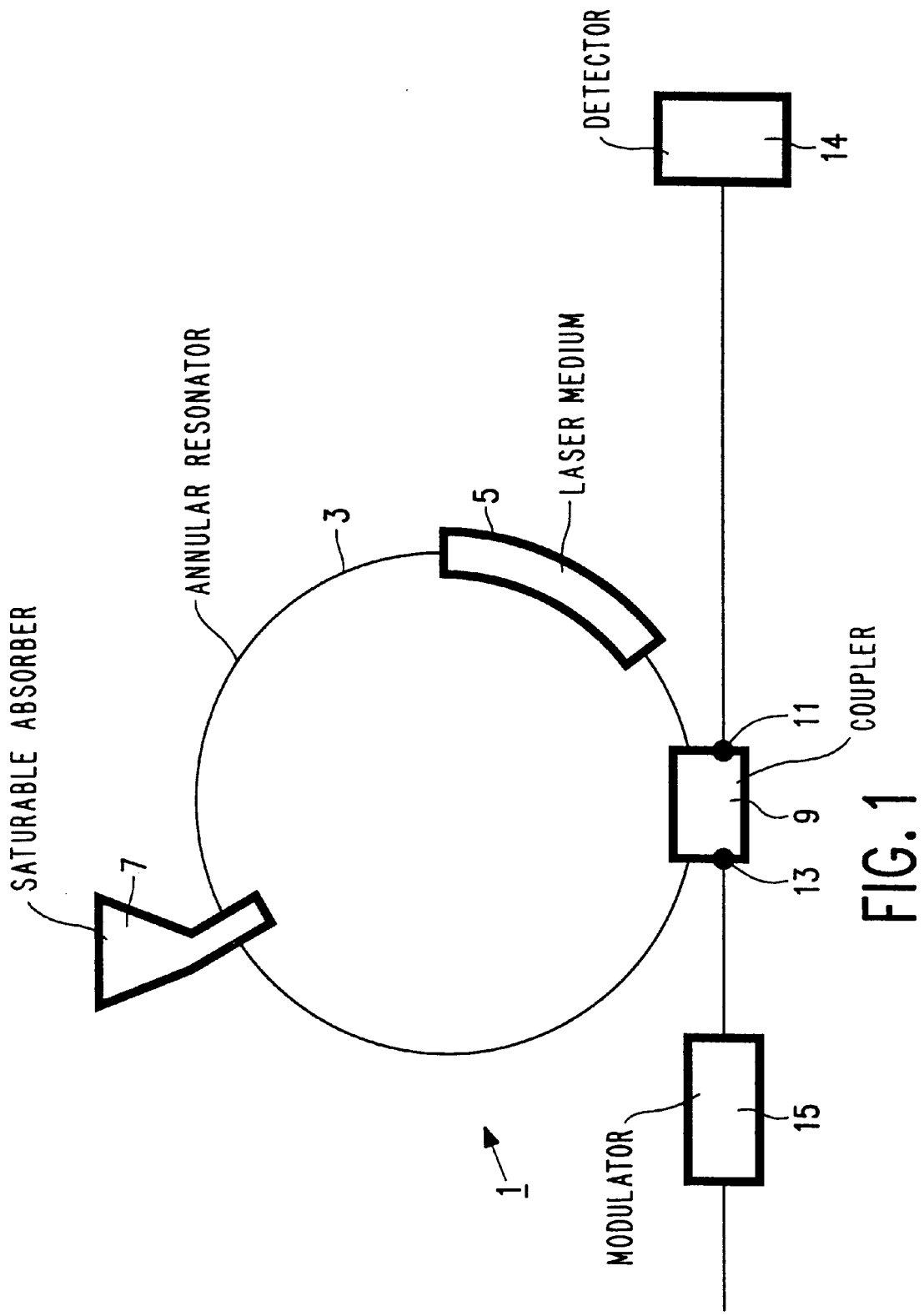
FIG. 1 shows an embodiment of a known ring laser.

The ring laser 1 shown in FIG. 1 is constituted by an annular resonator 3. The resonator 3 incorporates a laser medium 5, a saturable absorber 7 and a coupler 9. When the laser medium 5 is activated, radiation will be generated in the ring. The operating principle of a ring laser is based on the fact that the position of the absorber 7 in the ring 3 does not play a role. The coupler 9 provides the possibility of coupling out the pulses generated in the resonator 3. The coupler 9 is, for example a multimode interference coupler (MMI). One gate 11 of the coupler is connected to a detector 14, for example a photodetector, with which the pulse frequency of the generated pulse series can be measured, while the other gate 13 may be connected to a modulator 15. By means of this modulator 15, the pulse series generated by the ring laser may be provided with data.

The repetition frequency $f_{ref}$ of the ring laser is given by $$f_{ref} \approx c/n.L$$

in which c is the velocity of light in the medium of the resonator, n is the refractive index and L is the length of the resonator. From this it follows that the repetition frequency can be varied by changing the optical path length n.L. The optical path length n.L can be changed by changing, for example the charge carrier density by means of separate current injection into the ring, by means of radiation injection into the ring or by changing the temperature of the ring.

Figure 2:
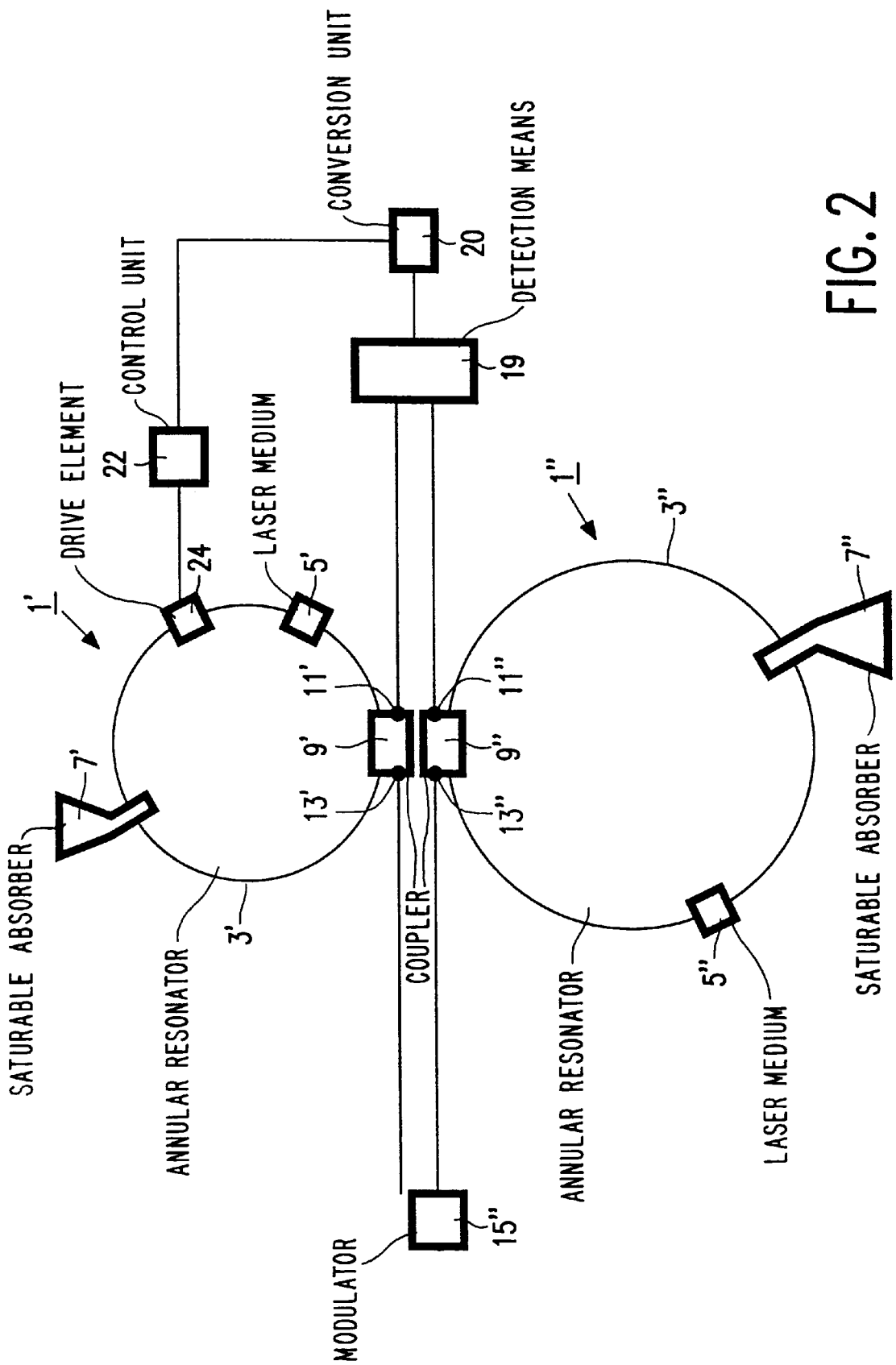
FIG. 2 shows an embodiment of an optical unit according to the invention, in which two ring lasers are synchronized with each other in a passive manner.

FIG. 2 shows an optical unit 17 which is provided with two ring lasers 1', 1". First gates 11" and 11' of both the first ring laser 1" and the second ring laser 1', respectively, are connected to detection means 19. The detection means 19 may be constituted, for example, by a photodetector which measures the difference frequency of the signals coming from each ring laser. A first requirement is that the signals of the two ring lasers to be synchronized with each other arrive simultaneously. Simultaneously is to be understood to mean within a given time interval in which the repetitive pattern of each ring laser is present. In fact, if the two ring lasers 1' and 1" have different repetition frequencies, the detection means may measure a difference frequency on the condition that both the pulses from ring laser 1' and the pulses from ring laser 1" are present within a given time interval. A second requirement is that the difference frequency falls within the bandwidth of the detection means. The detection means 19 may also be constituted by a unit which is capable of mixing two optical signals with each other. In such a unit, the two optical signals are combined, for example, by means of a coupler and mixed to one single signal which has a frequency which is equal to the difference frequency between the two mixed signals. Mixing of the two signals may be effected, for example, by means of a diode laser, a semiconductor laser amplifier or an optical fiber. The difference frequency may be converted into an electrical value by means of a conversion unit 20. The output of the conversion unit 20 is connected to the input of a control unit 22 by means of which a drive element 24 is controlled. The optical path length of the second ring laser 1' can be adapted by means of the drive element. If the optical path length is changed as a result of current injection, the control unit may be a current source and the drive element may be a segment. If the optical path length is influenced by radiation injection, the control unit may be a diode laser and the drive element may be a coupler. When the optical path length change is realized by changing the temperature of the resonator, the drive element is, for example a Peltier element and the control unit is the drive for this element.

Said manners of adapting the repetition frequencies of the two ring lasers to each other, notably by means of a photodetector or by means of an optical mixer, are passive.

The difference frequency measured by the detection means is the beat signal. The smaller this signal, the better the two frequencies $f_1$ and $f_2$ are adapted to each other. With reference to the value of this signal, the length of the resonator of at least one of the two ring lasers 1', 1", for example of laser 11", can be varied in order to derive this beat signal to zero. The repetition frequency of one of the ring lasers can be adapted by current injection, radiation injection or temperature change of the resonator 3' or 3". In this way, not only the repetition frequencies but also the phases of the two ring lasers are compared with each other.

The other gates 13', 13" serve as output gates and each have a different function. In the embodiment shown, the gate 13" is used for comparing the optical signal supplied by the ring laser with the electric signal, and the gate 13' is used, for example for connection to the detection means to which also a ring laser to be synchronized with ring laser 1' is connected.

The description hereinbefore deals with the way in which two optical signals are synchronized with each other. The following description will illustrate how the electric signal can be synchronized with an optical signal before it is synchronized with an optical signal having a higher repetition frequency. Synchronizing an optical and an electric signal may be effected both in a passive and in an active way, in contrast to synchronizing two optical signals, which is effected in a passive way only.

The gate of the ring laser having, for example the lowest frequency, in this case gate 13" of ring laser 1", is connected to an electric unit 15' which supplies an electric data signal, for example an electric modulator. The modulation frequency of the electric signal and the optical repetition frequency of the ring laser 1" can be synchronized with each other.

The optical signal supplied by the ring laser can be provided with the frequency of the electric signal by applying the frequency of the electric modulator directly to the resonator via a segment (current injection) without using feedback to adapt the electrical frequency to the optical frequency. In this way, the resonator is forced, as it were, to supply optical pulses at a given frequency. A condition is that the frequency of the electric signal and the frequency of the signal which the ring laser can generate itself are not too far apart.

The frequencies of the electric signal and the optical signal to be synchronized therewith may also be adapted to each other in a passive way. This may be effected by adapting the optical path length of the resonator 3" of the first ring 1". The signal which appears in this way at the output 27 of the optical unit 17 may be both an optical and an electric signal. If an electric signal is desired, a photodetector converting an optical pulse into an electric pulse may be present in the resonator 3" or in the connection between the ring laser 1" and the output 27 of the unit 17. The photodetector 16 may also be present outside the unit 17, as is the case in FIGS. 3(a) to 3(c). If that is the case, the optical signal is converted outside the unit into an electric signal. Subsequently, the signal from the ring laser 1" and the electric signal are combined in an electric mixer 21. A signal referred to as beat signal is then produced, which has a frequency which is equal to the difference frequency of the two combined signals and is measured by a detector 18. With reference to this beat signal, the length of the first ring laser 1" can be adapted in an active manner until said electric frequencies are substantially equal.

Figure 3A:
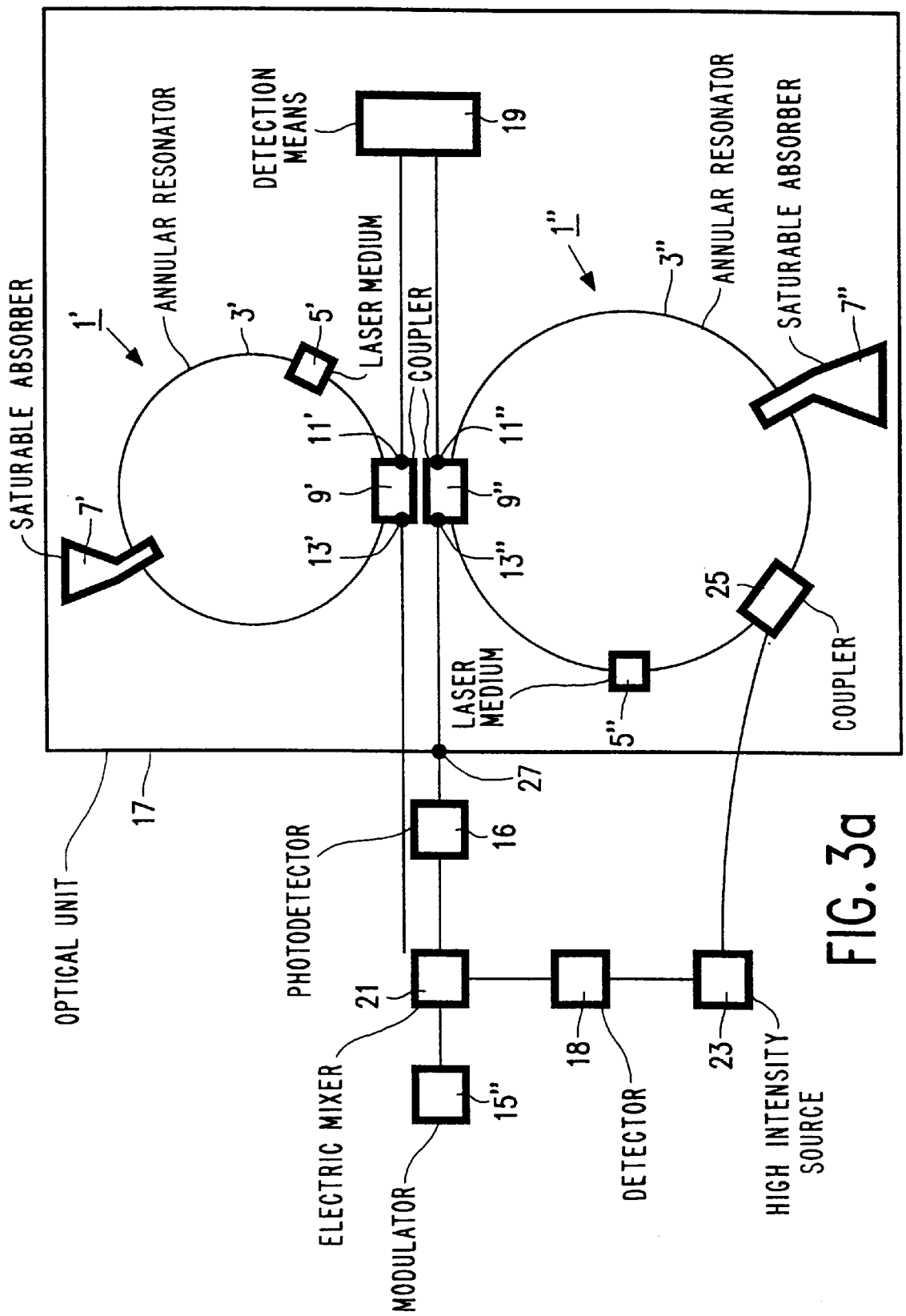
Figure 3C:
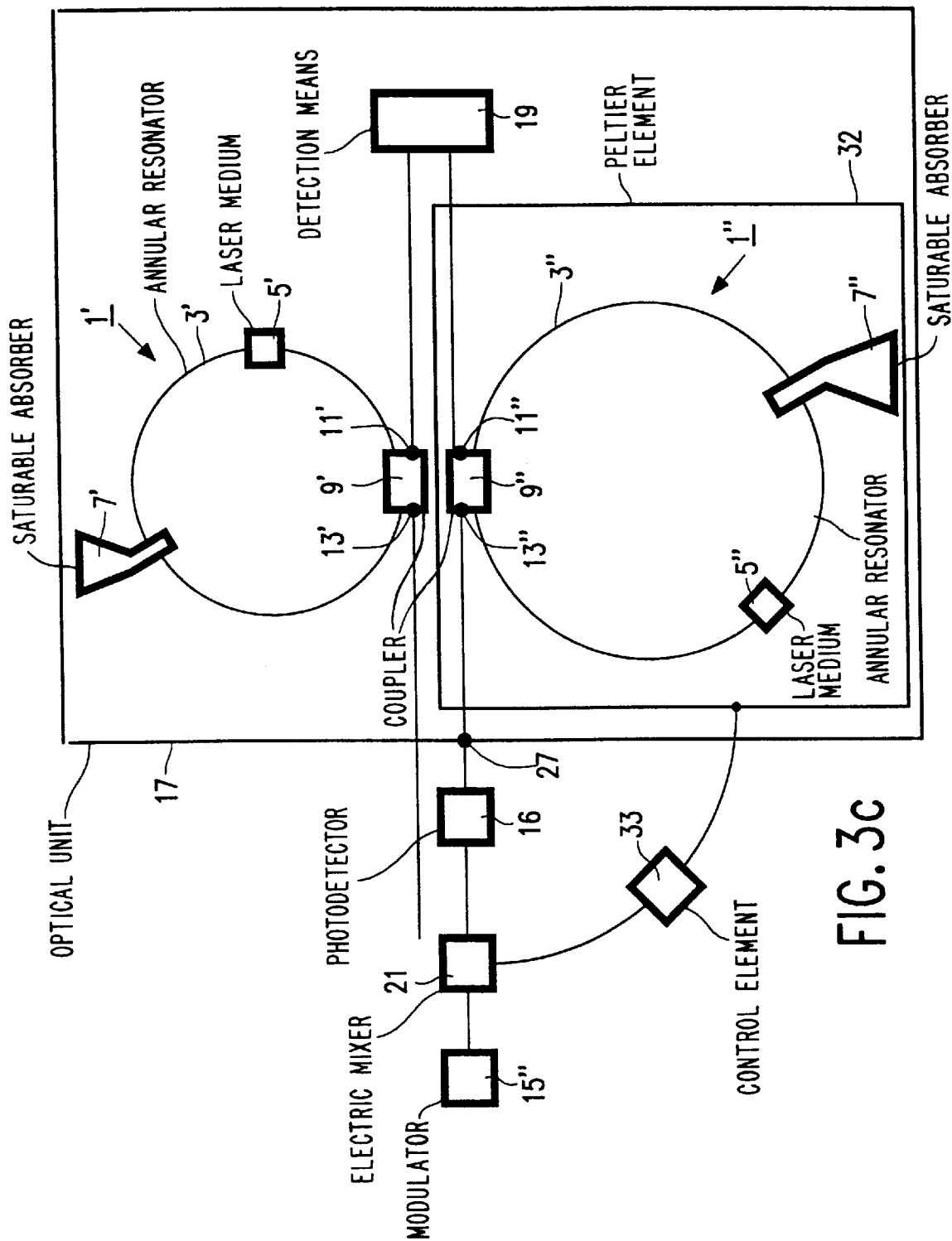

The optical path length of the first ring laser may be passively adapted to the frequency of the electric data signal in different manners. A first manner is illustrated in FIG. 3(a), consisting of connecting the output of the detector 18 measuring the beat signal to a high intensity source 23 whose radiation is injected into the resonator 3" via a coupler 25. Consequently, the charge carrier density in the resonator 3", and hence the repetition frequency of the ring laser 1" will change. Another possibility is to inject current into the resonator 3". The output of the detector 18 is then connected to the current source 29 which injects current via a segment 31, as is shown in FIG. 3(b). Yet another possibility is shown in FIG. 3(c), consisting of varying the temperature of the resonator 3", for example by means of a Peltier element 32 which is driven by means of a control element 33.

After the signal from one of the ring lasers has been synchronized with the electric data signal, other ring lasers having a higher repetition frequency can be synchronized with the ring laser. In this way, a high frequency clock signal will be formed which is synchronized with the original electric data signal. To this end, for example, the optical path length of the second, shorter resonator 3' should be adapted so as to ensure that the pulse series of the second ring laser 1' is synchronized with the pulse series of the first ring laser 1", as already described hereinbefore.

The second gate 13' of the second ring laser 1' should then be connected to detection means with which also a ring laser to be synchronized with ring laser 1' will be connected.

Since, in practice, the difference frequency between two ring lasers may be too large to be measured by an electric detector, such as a photodetector, multiples of the two frequencies $f_1$ and $f_2$ are compared with each other. At the instant when $k.f_1 \approx m.f_2$, in which k and m are integers, the signal having the higher repetition frequency is not only coupled to the pulse series of the ring laser 1" but also to the electric signal. Consequently, a clock signal which is synchronized with the electric signal but whose frequency is considerably raised appears at the gate 13' of the ring laser 1 having the highest frequency. The ring laser 1" can thus be locked with the electric signal. The same principle may be used for synchronizing the electric data signal with the optical signal generated by the ring laser coupled thereto.

The above will now be illustrated with reference to a numerical example. If, for example, $f_1=10$ GHz and $f_2=25$ GHz, then the difference frequency is 15 GHz. However, this frequency is too large to be measured by a photodetector. However, if it is ensured, by adapting the length of the rings, that, for example $5.f_1=2.f_2$, then $5.f_1-2.f_2 \approx 0$, so that the photodetector should only have a very small bandwidth to be able to measure this difference frequency.

What is claimed is:

1. An optical unit for synchronizing clock signals, said unit comprising at least two ring lasers to be synchronized with each other, each ring laser generating a repetitive optical pattern at a different repetition frequency $f_i$, and detection means coupled to said two ring lasers to simultaneously receive the optical patterns from the two ring lasers to be synchronized with each other and to compare said patterns, wherein the repetition frequency of at least one of the ring lasers is variable as a function of a signal from the detection means and, wherein the ring lasers to be synchronized have a characteristic such that it holds for repetition frequencies $f_1$ and $f_2$ of said ring lasers that $k.f_1 \approx m.f_2$, where k and m are integers.

2. An optical unit as claimed in claim 1, wherein one of the ring lasers is coupled to an electric pulse-generating unit.

3. An optical unit as claimed in claim 2, wherein an extent of radiation causing a charge carrier density change resulting in a change of the repetition frequency is injectable into the resonator of the ring laser which is coupled to the electric pulse-generating unit.

4. An optical unit as claimed in claim 2, wherein the resonator of the ring laser has an area in which current is injectable into the resonator.

5. An optical unit as claimed in claim 2, wherein the resonator is provided with means with which the temperature of the resonator is continuously variable.

6. An optical unit as claimed in claim 1, wherein the detection means comprise a photodetector for measuring a difference frequency between the repetition frequencies or between smallest common multiples of the repetition frequencies of the two ring lasers to be synchronized with each other, and the photodetector is connected to a conversion unit which in turn is coupled to a control unit for controlling a drive unit by means of which the optical path length of one of the ring lasers is variable.

7. An optical unit as claimed in claim 6, wherein an extent of radiation causing a charge carrier density change resulting in a change of the repetition frequency is injectable into the resonator of one of the ring lasers.

8. An optical unit as claimed in claim 6, wherein the resonator of one of the ring lasers has an area in which current is injectable into the resonator.

9. An optical unit as claimed in claim 6, wherein the resonator of one of the ring lasers is provided with means by which the temperature of the resonator is continuously variable.

10. An optical unit as claimed in claim 1, wherein the detection means comprise a unit in which the optical signals to be synchronized can be mixed to one signal having a frequency which is equal to the difference frequency between the signals to be mixed, said unit being connected to a conversion unit which in turn is coupled to a control unit for controlling a drive unit by means of which the optical path length of one of the ring lasers is variable.

11. A high-frequency carrier transmission system comprising an optical unit as claimed in claim 1.

* * * * *